US 007928260B2

(12) United States Patent
DeGonia et al.

(10) Patent No.: US 7,928,260 B2
(45) Date of Patent: Apr. 19, 2011

(54) SALT OF A SULFUR-CONTAINING, PHOSPHORUS-CONTAINING COMPOUND, AND METHODS THEREOF

(75) Inventors: David J. DeGonia, Midlothian, VA (US); Roger M. Sheets, Glen Allen, VA (US); Ronald L. Phillips, Richmond, VA (US)

(73) Assignee: Afton Chemical Corporation, Richmond, VA (US)

( * ) Notice: Subject to any disclaimer, the term of this patent is extended or adjusted under 35 U.S.C. 154(b) by 196 days.

(21) Appl. No.: 12/203,626

(22) Filed: Sep. 3, 2008

(65) Prior Publication Data

US 2008/0319216 A1  Dec. 25, 2008

Related U.S. Application Data

(63) Continuation of application No. 11/372,443, filed on Mar. 9, 2006, now abandoned.

(60) Provisional application No. 60/734,757, filed on Nov. 9, 2005.

(51) Int. Cl.
*C07F 9/02* (2006.01)

(52) U.S. Cl. ........................................ 558/161

(58) Field of Classification Search .................. 558/161
See application file for complete search history.

(56) References Cited

U.S. PATENT DOCUMENTS

| | | |
|---|---|---|
| 2,063,629 A | 12/1936 | Rosenmund |
| 2,224,695 A | 12/1940 | Prutton |
| 2,284,409 A | 5/1942 | Erath |
| 2,284,410 A | 5/1942 | Farmer |
| 2,447,288 A | 8/1948 | Smith et al. |
| 2,616,905 A | 11/1952 | Asseff et al. |
| 2,945,749 A | 7/1960 | Andress, Jr. |
| 3,087,936 A | 4/1963 | Le Suer |
| 3,172,892 A | 3/1965 | Le Suer et al. |
| 3,184,411 A | 5/1965 | Lowe |
| 3,192,162 A | 6/1965 | Bartlett et al. |
| 3,202,678 A | 8/1965 | Stuart et al. |
| 3,216,936 A | 11/1965 | Le Suer et al. |
| 3,219,666 A | 11/1965 | Norman et al. |
| 3,254,025 A | 5/1966 | Le Suer et al. |
| 3,272,746 A | 9/1966 | Le Suer et al. |
| 3,281,428 A | 10/1966 | Le Suer |
| 3,282,955 A | 11/1966 | Le Suer |
| 3,338,832 A | 8/1967 | Le Suer |
| 3,342,735 A | 9/1967 | Reed et al. |
| 3,344,069 A | 9/1967 | Stuebe |
| 3,403,102 A | 9/1968 | Le Suer et al. |
| 3,502,607 A | 3/1970 | Trapasso |
| 3,511,780 A | 5/1970 | Neblett et al. |
| 3,513,093 A | 5/1970 | Le Suer |
| 3,533,945 A | 10/1970 | Vogel |
| 3,658,836 A | 4/1972 | Vineyard |
| 3,682,819 A | 8/1972 | Morris et al. |
| 3,703,536 A | 11/1972 | Piasek et al. |
| 3,718,663 A | 2/1973 | Piasek et al. |
| 3,984,448 A | 10/1976 | Lippsmeier |
| 4,077,860 A | 3/1978 | Via |
| 4,234,435 A | 11/1980 | Meinhardt et al. |
| 4,348,291 A | 9/1982 | Shim |
| 4,370,247 A | 1/1983 | Ostyn |
| 4,431,552 A | 2/1984 | Salentine |
| 4,455,243 A | 6/1984 | Liston |
| 4,544,492 A | 10/1985 | Zinke et al. |
| 4,615,826 A | 10/1986 | Erdman |
| 4,648,980 A | 3/1987 | Erdman |
| 4,652,387 A | 3/1987 | Andress, Jr. et al. |
| 4,755,311 A | 7/1988 | Burjes et al. |
| 4,857,214 A | 8/1989 | Papay et al. |
| 4,900,460 A | 2/1990 | Cardis |
| 4,943,672 A | 7/1990 | Hamner et al. |
| 4,997,968 A | 3/1991 | Burjes et al. |
| 5,198,133 A | 3/1993 | Paypay |
| 5,240,622 A | 8/1993 | Nesvadba |
| 5,354,484 A | 10/1994 | Schwind et al. |
| 5,358,650 A | 10/1994 | Srinivasan et al. |
| 5,569,644 A | 10/1996 | Geibach et al. |
| 5,571,445 A | 11/1996 | Srinivasan et al. |
| 5,698,498 A | 12/1997 | Luciani et al. |
| 5,767,044 A | 6/1998 | Bigelow et al. |
| 5,882,505 A | 3/1999 | Wittenbrink et al. |
| 5,968,880 A | 10/1999 | Mathur et al. |
| 6,013,171 A | 1/2000 | Cook et al. |
| 6,080,301 A | 6/2000 | Berlowitz et al. |
| 6,096,691 A | 8/2000 | Conary et al. |

(Continued)

FOREIGN PATENT DOCUMENTS

EP  0459656  12/1991

(Continued)

OTHER PUBLICATIONS

Patani, George A. et al., Bioisosterism: A Rational Approach in Drug Design, Chem. Rev., 1996, 96, 3147-76, Department of Pharmaceutical Chemistry, College of Pharmacy, Rutgers. The State University of New Jersey, Piscataway, New Jersey 08855-0789. Kudelska, Wieslawa, Syntheis of glycosyl cyanides by the reaction of 1-S-phosphorothioates of carbohydrates with trimethylsilyl cyanide, Aeitschrift fuer Naturforschung, B: Chemical Sciences (1998), 53 (11), 1277-1280, CAS:130:110480.
Lopusinksi, Andrzej, et al., Reaction of dialkoxythiophosphoranesulfenyl chlorides with dialkyl trimethylsilyl phosphites. New stereoselective route to the unsymmetrical tetraalkyl dithiopyrophosphates. Preparation of diastereoisomeric 2-(trimethylsiloxy)-4 methyl-1, 3, 2 dioxaphosphorinanes, Phosphorus and Sulfur and the Related Elements, 1987, CAS:107:77911.
Zinke, Horst, et al., Lubricating Compositions, Eur. Pat. Appl., 29 pp. 1985, CAS:102:98177.
Via, Francis A., Photopolymerizable composition stabilized with ammonium salts of phosphorus acid and process, 1978, U.S., 9 pp. CODEN: USXXAM, CAS:89:25295.

(Continued)

*Primary Examiner* — Rei-tsang Shiao

(74) *Attorney, Agent, or Firm* — Luedeka, Neely & Graham, P.C.

(57) ABSTRACT

There is disclosed a salt of a sulfur-containing, phosphorus-containing compound. There is also disclosed a method of making the salt.

2 Claims, 1 Drawing Sheet

U.S. PATENT DOCUMENTS

| | | | |
|---|---|---|---|
| 6,096,940 | A | 8/2000 | Wittenbrink et al. |
| 6,103,099 | A | 8/2000 | Wittenbrink et al. |
| 6,165,949 | A | 12/2000 | Berlowitz et al. |
| 6,180,575 | B1 | 1/2001 | Nipe |
| 6,451,745 | B1 | 9/2002 | Ward |
| 6,528,458 | B1 | 3/2003 | Tagliamonte et al. |
| 6,562,765 | B1 | 5/2003 | Boffa |
| 6,844,300 | B2 | 1/2005 | Milner et al. |
| 6,890,890 | B2 | 5/2005 | Gahagan |
| 6,962,895 | B2 | 11/2005 | Scharf et al. |
| 2002/0010102 | A1 | 1/2002 | Koshima et al. |
| 2003/0096713 | A1 | 5/2003 | Schnur et al. |
| 2003/0166474 | A1 | 9/2003 | Winemiller et al. |
| 2004/0192564 | A1 | 9/2004 | Balasubramaniam et al. |
| 2004/0259743 | A1 | 12/2004 | Butke |
| 2005/0059562 | A1 | 3/2005 | Garmier |
| 2005/0059563 | A1 | 3/2005 | Sullivan et al. |
| 2005/0143266 | A1 | 6/2005 | Yagishita |
| 2005/0202979 | A1 | 9/2005 | Henly |
| 2007/0105728 | A1 | 5/2007 | Phillips et al. |

FOREIGN PATENT DOCUMENTS

| | | | |
|---|---|---|---|
| EP | 0578435 | | 1/1994 |
| EP | 1057883 | | 12/2000 |
| EP | 1195426 | | 4/2002 |
| EP | 1785476 | | 5/2007 |
| GB | 1268562 | | 3/1972 |
| GB | 1329978 | * | 9/1973 |
| WO | 8707638 | | 12/1987 |
| WO | 2005/028599 | | 3/2005 |

OTHER PUBLICATIONS

Milolajczyk, M. et al., Organophosphorus compounds. CLXX. Stereochemistry of organophosphorus cyclic compounds. I. Stereospecific synthesis of cis- and trans-2hydroxy-2-thio and (seleno)-4-methyl-1,3,2-dioxaphosphorinanes, 1973, CAS: 78:58286.

XP-002417703—Beilstein Registry No. 1908909; Jun. 29, 1989.

XP-002427219—Beilstein Registry No. 1859471; Jun. 29, 1989.

M. Michalska, J. Michalski, I. Orlich; "Glycosylation of Organic Thio- and Selenoacids of Phosphorus" Tetrahedron, vol. 34, 1972, pp. 617-622, XP002424356.

M. Mikolajczyk, J. Luczak; Tetrahedron, vol. 28, 1972, pp. 5411-5422, XP002417564.

D.A. Predvotilev, G.A. Savin, E.E. Nifantev; Journal of General Chemistry of the USSR, vol. 62, No. 11, 1992, pp. 2018-2025, XP000383103.

M. Mikolajczyk, P. Kietbasinski, A Suit: Tetrahedron, vol. 42, No. 16, 1986, pp. 4591-4601, XP002417562.

W. Kudelska, M. Michalska: Carbohydrate Research, vo. 83, 1980, pp. 43-49, XP002417563.

Olesiak et al, 2002, Synlett, No. 6, p. 967-971.

CA Reg No. 462104-21-8, entered into the STN database on Oct. 17, 2002.

Kudelska W. et al; "0,0-Dialkylphosphoro-Thioric and Dithioic Acid As Functionalising Reagents of Monosaccharides; Synthesis of 6-(Dialkoxyphosphinylthio)-Alpha-Glucofuranoses, and a New Route to 5, 6 Episulphides" Carbohydrate Research, Elsevier Scientific Publishing Company, Amsterdam, NL, vol. 83, 1980, pp. 43-49. XP002417563.

Said, Musa A., et al., "Reactivity of cyclic arsenites and phosphites: X-ray structures of bis (5,5-diemthyl-1,3,2-dioxarsenan-2-yl) ether and bis (2,4,8, 10-tetra-tert-butyl-12H-dibenzo[d,g] dioxarsenocin-6-yl)ether," J. Chem. Soc. Perkin Trans 1,22: 2945-51 (1995).

Oswald, Alexis A., "Synthesis of Cyclic Phosphorous Acid Esters by Transesteficiation," Can. J. Chem., 37:1498-1504 (1959).

Zwierzak, A., "Cyclic Organophosphorous Compounds. I. Synthesis and Infrared Spectral Studies of Cyclic Hydrogen Phosphites and Thiophosphites," Can. J. Chem., 45(21):2501-12 (1967).

Kumaraswamy, Sudha et al., "Synthesis of New a-Halogeno-and Vinylphosphonates Derived from 5,5-Dimethyl-1,3,2-dioxaphosphinan-2-one,"Synthesis, 2:207-12 (1997).

Edmundson, R.S., "Cyclic Organophosphorus Compounds—111 Some Sterically Hindered Pyrophosphates," Tetrahedron, 21:2379-87 (1965).

* cited by examiner

SALT OF A SULFUR-CONTAINING, PHOSPHORUS-CONTAINING COMPOUND, AND METHODS THEREOF

RELATED APPLICATIONS

This application claims the benefit of priority of U.S. Provisional Application No. 60/734,757, filed on Nov. 9, 2005 and is a continuation application of U.S. application Ser. No. 11/372,443, filed on Mar. 9, 2006 now abanonded.

DESCRIPTION OF THE DISCLOSURE

1. Field of the Disclosure

The present disclosure relates to a salt of a sulfur-containing, phosphorus-containing compound, and methods of making the salt.

2. Background of the Disclosure

The use of phosphorous-containing compounds for use in lubricant compositions is known. In particular, the phosphorous-containing compounds generally comprise linear alkyl chains. However, the problem with these compounds is that they are known to be thermally unstable at elevated temperatures in a fully formulated gear lubricant. A thermally unstable compound is more likely to prematurely decompose in the lubricant composition and would no longer provide a property, such as antiwear, to the lubricant composition.

Lubricant compositions, such as gear oils, typically are subjected to elevated temperatures and therefore it would be beneficial to provide a thermally stable compound that would not prematurely decompose at higher temperatures. A thermally stable compound would therefore remain in the lubricant composition for an extended period of time and provide the property, e.g., antiwear, to the composition over the extended period of time. What is needed is a compound that has the proper thermal stability to sustain its antiwear property.

SUMMARY OF THE DISCLOSURE

In accordance with the disclosure, there is disclosed an oil-soluble compound of formula (III):

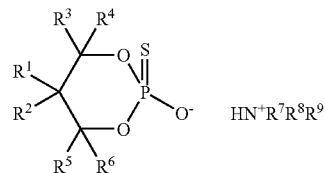

wherein $R^1$, $R^2$, $R^3$, $R^4$, $R^5$, $R^6$, $R^7$, $R^8$, and $R^9$ are independently selected from the group consisting of hydrogen, cyano, and hydrocarbyl groups comprising from about 1 to about 30 carbon atoms.

There is also disclosed a compound of formula (VI):

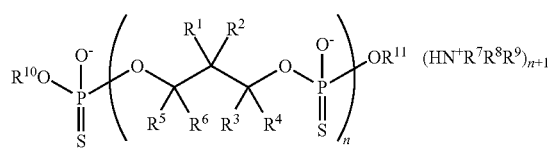

wherein n is an integer from 1 to 5; and wherein $R^1$, $R^2$, $R^3$, $R^4$, $R^5$, $R^6$, $R^7$, $R^8$, $R^9$, $R^{10}$, and $R^{11}$ are independently selected from the group consisting of hydrogen, cyano, and hydrocarbyl groups comprising from about 1 to about 30 carbon atoms.

In another aspect, there is disclosed a process of preparing a salt of sulfur-containing, phosphorus-containing compound comprising: providing a sulfur-containing compound, a nitrogen-containing compound and at least one compound of formula (I) and (IV):

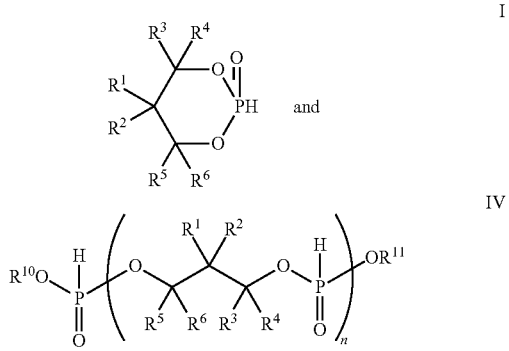

wherein n is an integer from 1 to 5; and wherein $R^1$, $R^2$, $R^3$, $R^4$, $R^5$, $R^6$, $R^{10}$, and $R^{11}$ are independently selected from the group consisting of hydrogen, cyano, and hydrocarbyl groups comprising from about 1 to about 30 carbon atoms.

Further, there is also disclosed a composition comprising a reaction product of a nitrogen-containing compound, a neopentyl glycol phosphite, and a sulfur-containing compound.

Additional objects and advantages of the disclosure will be set forth in part in the description which follows, and/or can be learned by practice of the disclosure. The objects and advantages of the disclosure will be realized and attained by means of the elements and combinations particularly pointed out in the appended claims.

It is to be understood that both the foregoing general description and the following detailed description are exemplary and explanatory only and are not restrictive of the disclosure, as claimed.

DESCRIPTION OF THE EMBODIMENTS

Figure 1:
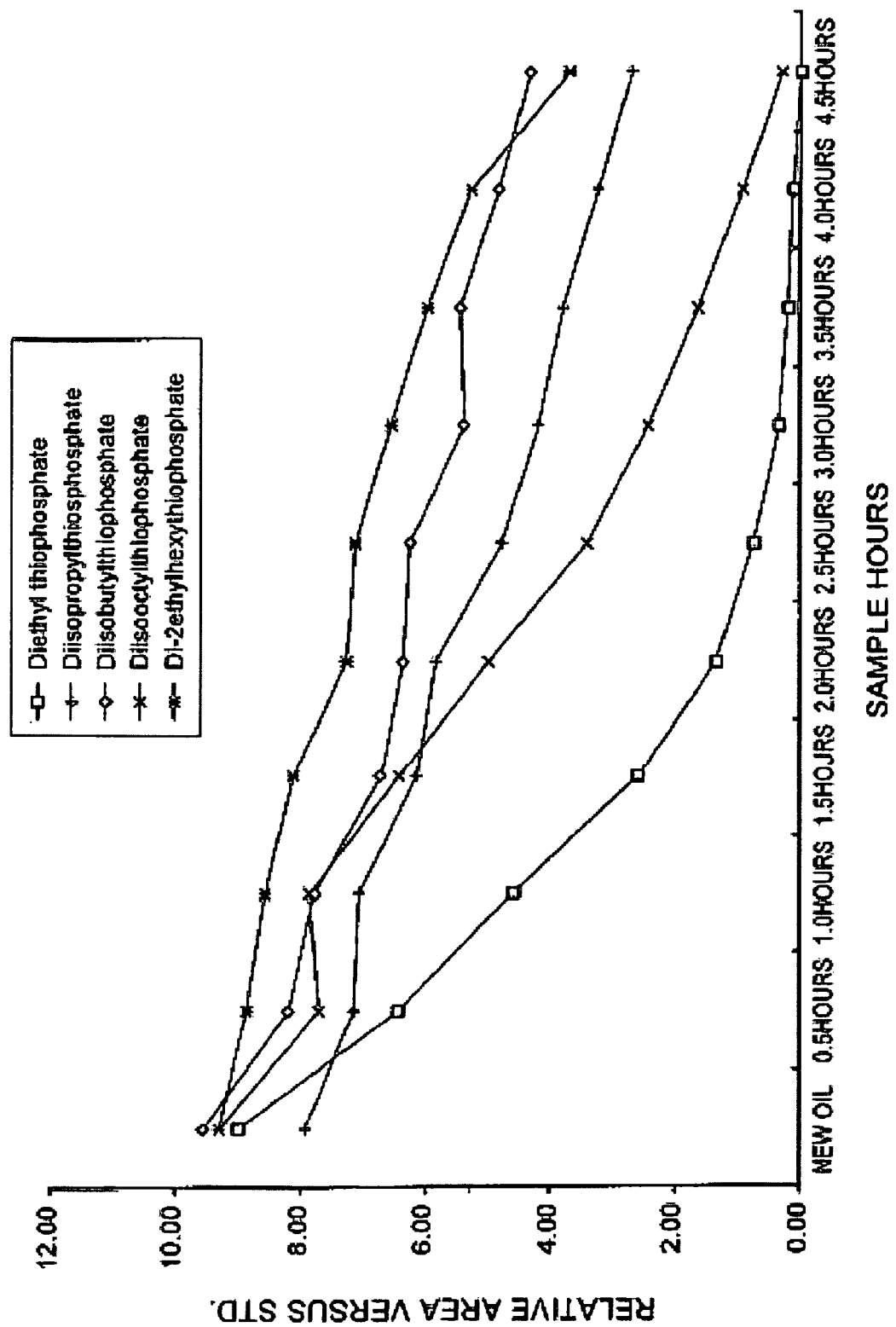
FIG. 1 is a graph illustrating the thermal stability of various phosphorus-containing species.

As used herein, the term "hydrocarbyl substituent" or "hydrocarbyl group" is used in its ordinary sense, which is well-known to those skilled in the art. Specifically, it refers to a group having a carbon atom directly attached to the remainder of the molecule and having predominantly hydrocarbon character. Examples of hydrocarbyl groups include:

(1) hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form an alicyclic radical);

(2) substituted hydrocarbon substituents, that is, substituents containing non-hydrocarbon groups which, in the context of this invention, do not alter the predominantly hydrocarbon substituent (e.g., halo (especially chloro and fluoro), hydroxy, alkoxy, mercapto, alkylmercapto, nitro, nitroso, and sulfoxy);

(3) hetero substituents, that is, substituents which, while having a predominantly hydrocarbon character, in the context of this invention, contain other than carbon in a ring or chain otherwise composed of carbon atoms. Heteroatoms include sulfur, oxygen, nitrogen, and encompass substituents as pyridyl, furyl, thienyl and imidazolyl. In general, no more than two, for example no more than one, non-hydrocarbon substituent will be present for every ten carbon atoms in the hydrocarbyl group; typically, there will be no non-hydrocarbon substituents in the hydrocarbyl group.

As used herein, the term "percent by weight", unless expressly stated otherwise, means the percentage the recited component represents to the weight of the entire composition.

In an aspect, there is provided a compound having at least one of improved antiwear and thermal stability. The compound can be a sulfur-containing, phosphorus-containing compound and/or its salt that can comprise steric hindrance to minimize and/or prevent decomposition of the compound at high temperatures. The disclosed compound and/or its salt can exhibit improved thermal stability and therefore remain in a lubricant composition longer than a composition that does not include steric hindrance. The steric hindrance can be present in any form, such as branching of hydrocarbyl chains, dependant hydrocarbyl chains, etc.

A phosphorus-containing compound, such as a phosphite or a phosphate can be used in the process disclosed herein. Methods of making both phosphites and phosphates are known. For example, phosphites can be made by reacting either phosphorous acid or different phosphites with various alcohols. Another synthesis method includes reacting phosphorus trichloride with an excess of alcohol. Moreover, cyclic phosphites can be made by transesterification of phosphites with glycols, which can result in a mixture of monomeric and polymeric products. See Oswald, Alexis A., "Synthesis of Cyclic Phosphorous Acid Esters by Transesterification," *Can. J. Chem.*, 37:1498-1504 (1959); and Said, Musa A., et al., "Reactivity of Cyclic Arsenites and Phosphites: X-ray structures of bis(5,5-dimethyl-1,3,2,-diosarsenan-2-yl)ether and bis(2,4,8,10-tetra-tert-butyl-12H-dibenzo[d,g][1,3,2]dioxarsenocin-6-yl)ether," *J. Chem. Soc.*, 22:2945-51 (1995), the disclosures of which are hereby incorporated by reference. Methods for making cyclic hydrogen thiophosphites are also known, such as by reacting a cyclic chlorophosphite with hydrogen sulfide in the presence of pyridine. See Zwierzak, A., "Cyclic organophosphorus compounds. I. Synthesis and infrared spectral studies of cyclic hydrogen phosphites and thiophosphites, *Can. J. Chem.*, 45:2501-12 (1967), the disclosure of which is hereby incorporated by reference.

In an aspect, the phosphite can be a di- or tri-hydrocarbyl phosphite. Each hydrocarbyl group can have from about 1 to about 24 carbon atoms, or from 1 to about 18 carbon atoms, or from about 2 to about 8 carbon atoms. Each hydrocarbyl group can be independently alkyl, alkenyl, aryl, and mixtures thereof. When the hydrocarbyl group is an aryl group, then it can contain at least about 6 carbon atoms; or from about 6 to about 18 carbon atoms. Non-limiting examples of the alkyl or alkenyl groups include propyl, butyl, hexyl, heptyl, octyl, oleyl, linoleyl, stearyl, etc. Non-limiting examples of aryl groups include phenyl, naphthyl, heptylphenol, etc. In an aspect, each hydrocarbyl group can be independently methyl, propyl, butyl, pentyl, hexyl, heptyl, oleyl or phenyl, for example methyl, butyl, oleyl or phenyl, and as a further example methyl, butyl, oleyl, or phenyl.

Non-limiting examples of useful phosphites include dibutyl hydrogen phosphonate, diisobutyl hydrogen phosphonate, dioleyl hydrogen phosphonate, di($C_{14-18}$) hydrogen phosphonate, triphenyl phosphite, a dihydrocarbyl phosphite, such as a compound of formula (I), and a polymeric phosphite, such as a compound of formula (IV), both shown below.

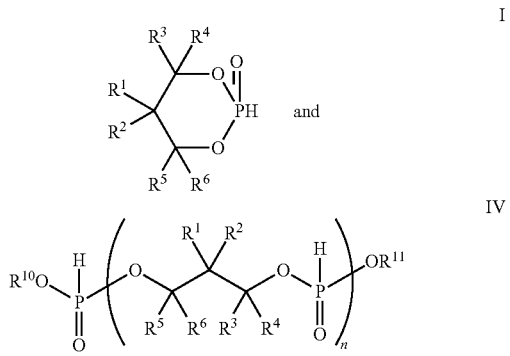

wherein n is an integer from about 1 to about 5; and wherein $R^1$, $R^2$, $R^3$, $R^4$, $R^5$, $R^6$, $R^{10}$, and $R^{11}$ can be independently selected from the group consisting of hydrogen, cyano, and hydrocarbyl groups comprising from about 1 to about 30 carbon atoms, for example from about 1 to about 20 carbon atoms, and as a further example from about 1 to about 10 carbon atoms. In an aspect, if n is an integer greater than about 5, it is believed, without being limited to any particular theory, that the repeating unit will not completely sulfurize.

In an aspect, in the compound of formula (I), $R^3$, $R^4$, $R^5$, and $R^6$ can be hydrogen; and $R^1$ and $R^2$ can be methyl. This compound is commonly referred to as neopentyl glycol phosphite (NPGP) and is registered with Chemical Abstracts Select under the designation CAS # 4090-60-2 (5,5-dimethyl-1,3,2-dioxaphosphorinan-2-one). In an aspect, in the compound of formula (IV), $R^1$ and $R^2$ can be methyl; $R^3$, $R^4$, $R^5$, and $R^6$ can be hydrogen; and $R^{10}$ and $R^{11}$ can be alkyl groups comprising from about 1 to about 6 carbon atoms. This compound is a polymeric by-product of the manufacturing process of neopentyl glycol phosphite.

The phosphorus-containing compound can also be at least one of a phosphoric acid ester or salt thereof, a reaction product of a phosphorus acid or anhydride and an unsaturated compound, and mixtures of two or more thereof.

A metal dithiophosphate can be prepared by reacting a metal base with at least one thiophosphorus acids, which can be mono- or dithiophosphorus acids.

The phosphorus acid or anhydride can be reacted with an unsaturated compound, including but not limited to, amides, esters, acids, anhydrides, and ethers.

In an aspect, the phosphorus-containing compound, such as a phosphite, can comprise various functional groups that increase the steric hindrance of the compound and therefore increase its resistance to thermal decomposition. In an aspect, the phosphorus-containing compound can be branched at the position beta to the oxygen atom in the hydrocarbyl chain. It is believed that branching at this beta carbon can change, e.g., can improve, the thermal stability of the phosphorus-containing compound in a lubricant composition.

Moreover, the phosphorus-containing compound can be made using components that would increase the resultant compound's steric hindrance. For example, the alcohol used to make, for example, the phosphite can be a beta-branched alcohol. Non-limiting examples of beta-branched alcohols include isobutanol, 2-ethylhexanol, neopentyl glycol, neopentyl alcohol, pristanol, and methyl isobutyl carbinol (MIBC).

The disclosed phosphorus-containing compound can be used as a starting material to yield a salt of a sulfur-containing, phosphorus-containing compound. In an aspect, the process for making a salt of a sulfur-containing, phosphorus-containing compound can comprise providing a phosphorus-containing compound, such as those described above, a sulfur-containing compound, and a nitrogen-containing compound to yield the salt of the sulfur-containing, phosphorus-containing compound. In another aspect, there is contemplated a composition comprising a reaction product of a nitrogen-containing compound; a phosphorus-containing compound, such as a neopentyl glycol phosphite; and a sulfur-containing compound. The reaction product can provide improved antiwear properties as compared to a non-sulfur-containing, phosphorus-containing compound.

The sulfur-containing compound can be any compound that comprises free and/or active sulfur. Non-limiting examples of sulfur-containing compounds include sulfurized animal or vegetable fats or oils, sulfurized animal or vegetable fatty acid esters, fully or partially esterified esters of trivalent or pentavalent acids of phosphorus, sulfurized olefins, dihydrocarbyl polysulfides, sulfurized Diels-Alder adducts, sulfurized dicyclopentadiene, sulfurized or co-sulfurized mixtures of fatty acid esters and monounsaturated olefin, co-sulfurized blends of fatty acid, fatty acid ester and α-olefin, functionally-substituted dihydrocarbyl polysulfides, thio-aldehydes, thio-ketones and derivatives thereof (e.g., acids, esters, imines, or lactones), epithio compounds, sulfur-containing acetal derivatives, co-sulfurized blends of terpene and acyclic olefins, polysulfide olefin products, and elemental sulfur.

In an aspect, the sulfur-containing compound can be made by reacting an olefin, such as isobutene, with sulfur. The product, e.g., sulfurized isobutylene or sulfurized polyisobutylene, typically has a sulfur content of 10 to 55%, for example 30 to 50% by weight. A wide variety of other olefins or unsaturated hydrocarbons, e.g., isobutene dimer or trimer, can be used to form such sulfur-containing compounds.

In another aspect, polysulfides composed of one or more compounds represented by the formula: $R^{20}-S_x-R^{21}$ where $R^{20}$ and $R^{21}$ can be hydrocarbyl groups each of which can contain from about 3 to about 18 carbon atoms and x can be in the range of from about 2 to about 8, for example in the range of from about 2 to about 5, and as a further example can be 3. The hydrocarbyl groups can be of widely varying types such as alkyl, cycloalkyl, alkenyl, aryl, or aralkyl. Tertiary alkyl polysulfides such as di-tert-butyl trisulfide, and mixtures comprising di-tert-butyl trisulfide (e.g., a mixture composed principally or entirely of the tri, tetra-, and pentasulfides) can be used. Examples of other useful dihydrocarbyl polysulfides include the diamyl polysulfides, the dinonyl polysulfides, the didodecyl polysulfides, and the dibenzyl polysulfides.

The sulfur-containing compound can be used in at least an equimolar or greater amount per equivalent of phosphorus-containing compound. In an aspect, from about 1 to about 1.5 molar equivalents of the sulfur-containing compound can be used.

The disclosed process can include the use of solvents. The solvent can be any inert fluid substance in which at least one of the reactants is soluble or the product is soluble. Non-limiting examples include benzene, toluene, xylene, n-hexane, cyclohexane, naphtha, diethyl ether carbitol, dibutyl ether dioxane, chlorobenzene, nitrobenzene, carbon tetrachloride, chloroform, polyalphaolefin, base oil, and process oil.

The disclosed process further comprises providing a nitrogen-containing compound. The nitrogen-containing compound can help promote the sulfurization of the disclosed phosphorus-containing compound and/or can help neutralize any acids. Any nitrogen-containing compound can be used so long as it is soluble in the lubricating composition which can comprise a base oil. Non-limiting examples of the nitrogen-containing compound include an amide, an amine, and a heterocyclic compound comprising a basic nitrogen, such as pyridine. In an aspect, the nitrogen-containing compound is an amine, which can be primary, secondary, or tertiary.

In an aspect, the hydrocarbyl amines can be primary hydrocarbyl amines comprising from about 4 to about 30 carbon atoms in the hydrocarbyl group, and for example from about 8 to about 20 carbon atoms in the hydrocarbyl group. The hydrocarbyl group can be saturated or unsaturated. Representative examples of primary saturated amines are those known as aliphatic primary fatty amines. Typical fatty amines include alkyl amines such as n-hexylamine, n-octylamine, n-decylamine, n-dodecylamine, n-tetradecylamine, n-pentadecylamine, n-hexadecylamine, n-octadecylamine (stearyl amine), etc. These primary amines are available in both distilled and technical grades. While the distilled grade can provide a purer reaction product, amides and imides can form in reactions with the amines of technical grade. Also suitable are mixed fatty amines.

In an aspect, the amine salts of the disclosed compounds can be those derived from tertiary-aliphatic primary amines having at least about 4 carbon atoms in the alkyl group. For the most part, they can be derived from alkyl amines having a total of less than about 30 carbon atoms in the alkyl group.

Usually the tertiary aliphatic primary amines are monoamines represented by the formula

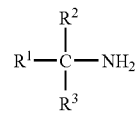

wherein $R^1$, $R^2$, and $R^3$ can be the same or different and can be a hydrocarbyl group containing from about one to about 30 carbon atoms. Such amines are illustrated by tertiary-butyl amine, tertiary-hexyl primary amine, 1-methyl-1-amino-cyclohexane, tertiary-octyl primary amine, tertiary-decyl primary amine, tertiary-dodecyl primary amine, tertiary-tetradecyl primary amine, tertiary-hexadecyl primary amine, tertiary-octadecyl primary amine, tertiary-tetracosanyl primary amine, tertiary-octacosanyl primary amine.

Mixtures of amines are also useful for the purposes of this disclosure. Illustrative of amine mixtures of this type can be a mixture of $C_8$-$C_{16}$ tertiary alkyl primary amines and a similar mixture of $C_{14}$-$C_{24}$ tertiary alkyl primary amines. The tertiary alkyl primary amines and methods for their preparation are well known to those of ordinary skill in the art and, therefore, further discussion is unnecessary. The tertiary alkyl primary amine useful for the purposes of this disclosure and methods for their preparation are described in U.S. Pat. No. 2,945,749, which is hereby incorporated by reference for its teaching in this regard.

Primary amines in which the hydrocarbon chain comprises olefinic unsaturation also can be quite useful. Thus, the R groups can contain at least one olefinic unsaturation depending on the length of the chain, usually no more than one double bond per 10 carbon atoms. Representative amines are dodecenylamine, myristoleylamine, palmitoleylamine, oleylamine and linoleylamine.

Secondary amines include dialkylamines having two of the above alkyl groups including fatty secondary amines, and also mixed dialkylamines where R' can be a fatty amine and R" can be a lower alkyl group (1-9 carbon atoms) such as methyl, ethyl, n-propyl, i-propyl, butyl, etc., or R" can be an alkyl group bearing other non-reactive or polar substituents (CN, alkyl, carbalkoxy, amide, ether, thioether, halo, sulfoxide, sulfone). The fatty polyamine diamines can include mono- or dialkyl, symmetrical or asymmetrical ethylene diamines, propane diamines (1,2, or 1,3), and polyamine analogs of the above. Suitable fatty polyamines include N-coco-1,3-diaminopropane, N-soyaalkyl trimethylenediamine, N-tallow-1,3-diaminopropane, and N-oleyl-1,3-diaminopropane.

In an aspect, the nitrogen-containing compound is not triethyl amine or cyclohexyl amine.

The nitrogen-containing compound can be provided in any amount necessary to drive the disclosed process to completion, i.e., if enough nitrogen-containing compound is not present then the phosphorus-containing compound does not completely sulfurize. In an aspect, the nitrogen-containing compound can be provided in an amount ranging from about 0.05 to about 2, and for example from about 1 to about 1.5 molar equivalent per equivalent of phosphorus-containing compound.

The disclosed process can occur at room about temperature (23° C.) or above, for example at least about 50° C., and as a further example ranging from about 50° C. to about 90° C. Generally, mixing at room temperature for a period ranging from about 1 minute to about 8 hours can be sufficient.

The resultant compound can be a compound of at least one formulae (III) and (VI), both shown below.

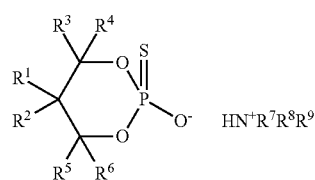

III

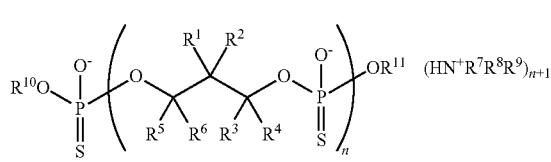

VI wherein n is an integer from 1 to 5; and wherein $R^1$, $R^2$, $R^3$, $R^4$, $R^5$, $R^6$, $R^7$, $R^8$, $R^9$, $R^{10}$, and $R^{11}$ can be independently selected from the group consisting of hydrogen, cyano, and hydrocarbyl groups comprising from about 1 to about 30 carbon atoms, for example from about 1 to about 20 carbon atoms, and as a further example from about 1 to about 10 carbon atoms.

In an aspect, in the compound of formula (III), $R^1$, $R^4$, $R^5$, $R^6$, $R^7$, and $R^8$ can be hydrogen; $R^1$ and $R^2$ can be methyl; and $R^9$ can be a tertiary $C_{12-14}$ alkyl group. In an aspect, in the compound of formula (VI), $R^1$ and $R^2$ can be methyl; $R^3$, $R^4$, $R^5$, $R^6$, $R^7$, and $R^8$ can be hydrogen; $R^9$ can be a tertiary $C_{12-14}$ alkyl group; and $R^{10}$ and $R^{11}$ can be alkyl groups comprising from about 1 to about 6 carbon atoms.

Methods for the preparation of such salts are well known and reported in the literature. See for example, U.S. Pat. Nos. 2,063,629; 2,224,695; 2,447,288; 2,616,905; 3,984,448; 4,431,552; 5,354,484; Pesin et al, Zhurnal Obshchei Khimii, 31(8): 2508-2515 (1961); and PCT International Application Publication No. WO 87/07638, the disclosures of which are hereby incorporated by reference.

The salt of the sulfur-containing, phosphorus-containing compound can be formed separately and then added to a lubricating or functional fluid composition. Alternatively, the salt can be formed when the phosphorus-containing compound, such as the disclosed phosphite, is blended with other components to form the lubricating or functional fluid composition. However, if the salt is formed in situ then it is important to restrict the acids, such as anti-rust components, present in the composition because the acids can react with the nitrogen-containing compound and stop the sulfurization and salt formations.

The salt of a sulfur-containing, phosphorus-containing compound can be oil-soluble, i.e., the hydrocarbyl chains of the salt can be of sufficient length, such as at least six carbon atoms, so that the resultant compound is soluble in a formulated composition. The incorporation of hydrophobic groups can lead to an increase in solubility in a non-polar media. Non-limiting examples of a salt of a sulfur-containing, phosphorus-containing compound include diisobutyl thiophosphoric acid $C_{8-16}$ tertiary alkyl primary amine salt, di-2-ethylhexyl-thiophosphoric acid $C_{8-16}$ tertiary alkyl primary amine salt, and neopentyl glycol thiophosphoric acid $C_{8-16}$ tertiary alkyl primary amine salt. In an aspect, there is contemplated a salt of a dithiophosphoric acid.

EXAMPLES

Example 1

Sulfurization of Neopentyl Glycol Phosphite (NPGP) with a Branched Amine

1 L reactor equipped with a pressure equalizing addition funnel was charged with sulfur (53.3 g, 1.7 mol), a nitrogen-containing compound (PRIMENE® 81R) (320.7 g, 1.7 mol) and 4 cSt polyalphaolefin (375.6 g). The addition funnel was then charged with liquid NPGP (250.04 g, 1.7 mol). The NPGP is a solid at standard conditions and has a melting point ranging from about 60° C. to about 65° C. The additional funnel was heated to avoid solidification.

With stirring and under a blanket of nitrogen, the NPGP was added to the reactor while keeping the mass temperature from about 60 to about 90° C. The rate of the addition was governed by the ability of the reaction system to control the exotherm. The process is exothermic; therefore, cooling of the reaction mass during the addition was required. After the addition was completed, the reaction mixture was stirred at 70 to 90° C. for 2 to 6 hours until all of the sulfur was consumed.

The observed P-31 NMR chemical shift (ppm) of the sulfurized NPGP was 52.96.

As discussed above, any sulfur-containing compound can be used as the sulfur source so long as there is free and active sulfur. For example, it is envisaged that the following process would also make the disclosed compounds.

A 2 L reactor equipped with a pressure equalizing addition funnel can be charged with 2,5-bis-(t-nonyidithio)-1,3,4-thiadiazole (396.8 g, 0.85 mol), PRIMENE®81R (320.7 g, 1.7 mol) and 4Cst PAO (375.6 g). The addition funnel could then be charged with liquid NPGP (250.04 g, 1.7 mol). The NPGP is a solid at standard conditions and has a melting point ranging from about 60° C. to about 65° C. to melt. The additional funnel could be heated to avoid solidification.

With stirring and under a blanket of nitrogen, the NPGP should be added to the reactor while keeping the mass temperature from about 60 to about 90° C. The rate of the addition is governed by the ability of the reaction system to control the exotherm. After the addition is completed, the reaction mixture can be stirred at from about 70 to about 90° C. for about 2 hours.

Example 2

Sulfurization of Neopentyl Glycol Phosphite (NPGP) with a Linear Amine

A 1 L reactor equipped with a pressure equalizing addition funnel can be charged with sulfur (53.3 g, 1.7 mol), a nitrogen-containing compound (ARMEEN® OL) (464.1 g, 1.7 mol) and 4 cSt polyalphaolefin (375.6 g). The addition funnel can then be charged with liquid NPGP (250.04 g, 1.7 mol). The NPGP is a solid at standard conditions and has a melting point ranging from about 60° C. to about 65° C. to melt. The additional funnel should be heated to avoid solidification. With stirring and under a blanket of nitrogen, the NPGP can be added to the reactor while keeping the mass temperature from about 60 to 90° C. The rate of the addition can be governed by the ability of the reaction system to control the exotherm. The process is exothermic; therefore, cooling of the reaction mass during the addition can be required. After the addition is complete, the reaction mixture can be stirred at from about 70 to about 90° C. for about 2 to about 6 hours until all of the sulfur is consumed.

Example 3

Antiwear Effectiveness

The potential of the antiwear effectiveness was measured by the duration of the phosphorous species at an elevated temperature. A fully formulated gear fluid was placed in a heated bath at about 325° F. Aliquots of the fully formulated gear fluid were pulled at timed intervals and the $^{31}$Phosphorus Nuclear Magnetic Resonance (NMR) spectrum was taken. The phosphorus species observed in the $^{31}$Phosphorus NMR spectrum were plotted versus time and thermal decomposition. A profile for the phosphorus antiwear species was created. The rate or amount of decomposition of the phosphorus species was dependant on the chemical structure of the hydrocarbyl chain. Examples of the phosphorus antiwear components were the dialkylthiophosphoric acid amine salts. The changes to the alkyl branching changed the thermal decomposition rate of the dialkylthiophosphoric acid amine salts in the heat bath at 325° F. The thermal stabilization was most effective when the beta carbon to the phosphorus-oxygen bond was branched with methyl or a high homolog alkyl group. Examples of the increased stability as demonstrated by a shallower slope are shown in FIG. 1.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," include plural referents unless expressly and unequivocally limited to one referent. Thus, for example, reference to "an antioxidant" includes two or more different antioxidants. As used herein, the term "include" and its grammatical variants are intended to be non-limiting, such that recitation of items in a list is not to the exclusion of other like items that can be substituted or added to the listed items.

While particular embodiments have been described, alternatives, modifications, variations, improvements, and substantial equivalents that are or can be presently unforeseen can arise to applicants or others skilled in the art. Accordingly, the appended claims as filed and as they can be amended are intended to embrace all such alternatives, modifications variations, improvements, and substantial equivalents.

What is claimed is:

1. A compound of formula (VI):

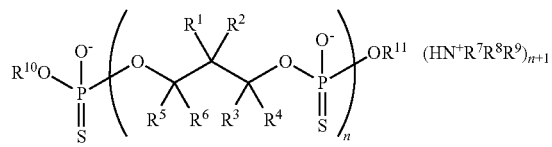

VI wherein n is an integer from 2 to 5; and
wherein $R^1$, $R^2$, $R^3$, $R^4$, $R^5$, $R^6$, $R^7$, $R^8$, $R^9$, $R^{10}$, and $R^{11}$ are independently selected from the group consisting of hydrogen, cyano, and hydrocarbyl groups comprising from about 1 to about 30 carbon atoms.

2. The compound of claim 1, wherein $R^1$ and $R^2$ are methyl, $R^3$, $R^4$, $R^5$, $R^6$, $R^7$, and $R^8$ are hydrogen; $R^9$ is a tertiary $C_{12\text{-}14}$ alkyl group; and $R^{10}$ and $R^{11}$ are alkyl groups comprising from about 1 to about 6 carbon atoms.

* * * * *